(12) United States Patent
Kanyuh

(10) Patent No.: US 11,447,707 B2
(45) Date of Patent: Sep. 20, 2022

(54) PARAFFIN DEHYDROGENATION PROCESS AND APPARATUS

(71) Applicant: UOP LLC, Des Plaines, IL (US)

(72) Inventor: Adam J Kanyuh, Streamwood, IL (US)

(73) Assignee: UOP LLC, Des Plaines, IL (US)

( * ) Notice: Subject to any disclaimer, the term of this patent is extended or adjusted under 35 U.S.C. 154(b) by 23 days.

(21) Appl. No.: 17/131,453

(22) Filed: Dec. 22, 2020

(65) Prior Publication Data

US 2022/0195319 A1  Jun. 23, 2022

(51) Int. Cl.
*C10G 49/22* (2006.01)
*F25J 3/02* (2006.01)

(52) U.S. Cl.
CPC ............ *C10G 49/22* (2013.01); *F25J 3/0204* (2013.01); *F25J 3/0252* (2013.01); *C10G 2300/1037* (2013.01); *C10G 2300/4081* (2013.01); *C10G 2400/20* (2013.01); *F25J 2205/10* (2013.01); *F25J 2230/20* (2013.01); *F25J 2230/32* (2013.01); *F25J 2230/60* (2013.01)

(58) Field of Classification Search
CPC ...... F25J 3/0204; F25J 3/0252; F25J 2230/32; F25J 2230/60
See application file for complete search history.

(56) References Cited

U.S. PATENT DOCUMENTS

| | | | | |
|---|---|---|---|---|
| 4,381,418 A | * | 4/1983 | Gewartowski | C07C 5/333 585/654 |
| 5,414,188 A | * | 5/1995 | Ha | C07C 7/09 585/800 |
| 5,457,256 A | * | 10/1995 | Mitariten | C07C 11/02 585/655 |
| 2013/0158327 A1 | * | 6/2013 | Leonard | C07C 5/333 585/654 |

* cited by examiner

*Primary Examiner* — Randy Boyer
(74) *Attorney, Agent, or Firm* — Paschall & Associates, LLC; James C. Paschall

(57) ABSTRACT

A process for recovering hydrogen from dehydrogenation reactor effluent is disclosed. A feed stream comprising hydrocarbons and hydrogen to a dehydrogenation reactor maintained at dehydrogenation conditions to provide a dehydrogenation reactor effluent. The dehydrogenation reactor effluent is passed to a cold box separation unit to provide a liquid hydrocarbon product stream and a recycle hydrogen stream. A return portion of the recycle hydrogen stream is passed to the reactor effluent compressor. The subject matter disclosed improved process and apparatus which enables the paraffin dehydrogenation reactor to run at reduced $H_2$/HC ratio without requiring an investment in a resized compressor or resized turboexpanders or separators in the cold box.

19 Claims, 1 Drawing Sheet

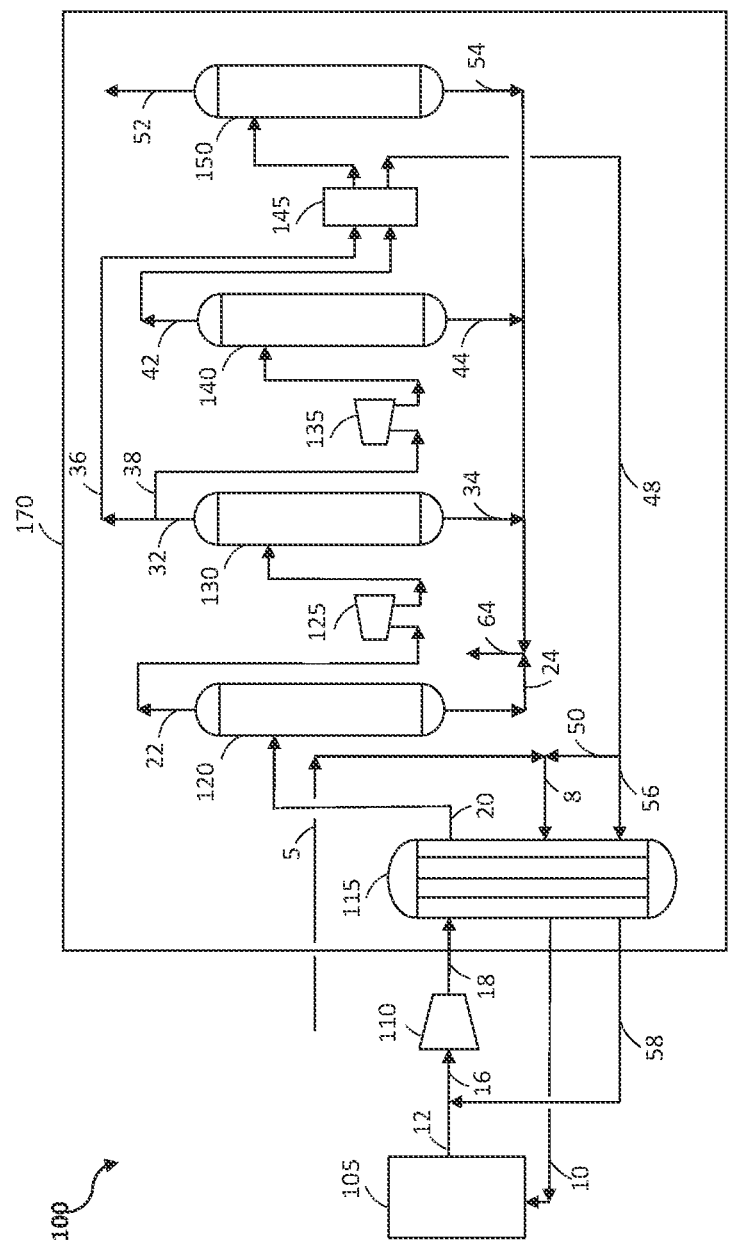

PARAFFIN DEHYDROGENATION PROCESS AND APPARATUS

FIELD

The field relates to paraffin dehydrogenation. More particularly, the field relates to hydrogen management in paraffin dehydrogenation.

BACKGROUND

Dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. In particular, demand of propylene in the petrochemical industry has grown substantially due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. One route for producing propylene is dehydrogenation of propane.

A process for the conversion of paraffins to olefins involves passing a paraffin feed stream over a highly selective catalyst, where the paraffin is dehydrogenated to the corresponding olefin and produce a dehydrogenation reactor effluent. Cooling and separation of the dehydrogenation reactor effluent into a hydrocarbon-rich fraction and a hydrogen-rich vapor fraction, part of which is non-recycled net off gas, is provided in a separation zone. The separation zone typically includes a reactor effluent compressor (REC), and a series of turbo expanders and separation vessels commonly referred to as a cold box.

In paraffin dehydrogenation reactor, hydrogen is commonly co-fed to minimize the amount of carbonaceous material deposited on the catalyst and to improve catalyst stability. Practically, the amount of hydrogen co-feed is represented as the hydrogen to hydrocarbon ($H_2$/HC) ratio, which is calculated by dividing the hydrogen molar flow rate by the hydrocarbon molar flowrate. While hydrogen decreases coking on the catalyst, it also changes the equilibrium conversion of paraffin to the desired olefin at a given temperature and pressure. Thus, there is a trade-off between minimizing catalyst coking and maximizing conversion.

Based on recent developments, running at reduced H2/HC ratio enables the reactor inlet temperatures (RITs) to be lowered which in turn reduces fouling and increases time between reactor turnarounds. While reducing the $H_2$/HC ratio in the dehydrogenation reactor results in improved product olefin yield, it creates challenges for the existing REC and cold box designs which rely on the hydrogen present within the dehydrogenation reactor effluent stream. Therefore, there is a need for a modified process with improved hydrogen management.

SUMMARY

We have found an improved process for managing $H_2$/HC ratio during a paraffin dehydrogenation process which enables the reactor effluent compressor and cold box turbo expanders to operate at the same $H_2$/HC ratio as the original design and at the same time enables the paraffin dehydrogenation reactor to run at a reduced $H_2$/HC ratio. A return hydrogen stream is recovered from the reactor effluent and returned to the reactor effluent compressor and cold box turbo expanders to enable them to run at the same $H_2$/HC ratio despite operating the dehydrogenation reactor at a reduce ratio.

The process comprises passing a feed stream comprising hydrocarbons and hydrogen to a dehydrogenation reactor at dehydrogenation conditions to provide a dehydrogenation reactor effluent. The amount of hydrogen co-feed is represented as the hydrogen to hydrocarbon ($H_2$/HC) ratio, which is calculated by dividing the hydrogen molar flow rate by the hydrocarbon molar flowrate. The dehydrogenation reactor effluent is passed to a reactor effluent compressor to provide a compressed hydrocarbon stream. The compressed hydrocarbon stream is passed to a cold box separation unit to provide an olefin stream and a recycle hydrogen stream. A return portion of the recycle hydrogen stream is passed to the reactor effluent compressor.

The cold box separation unit comprises of a cold combined feed exchanger, multiple separation vessels, expanders and coolers. The recycle hydrogen stream is split upstream of the cold combined feed exchanger into a return portion and a charge portion of the recycle hydrogen stream wherein the return portion is 30-50 wt % of the recycle hydrogen stream and the charge portion is 50-70 wt % of the recycle hydrogen stream.

These and other features, aspects, and advantages of the present disclosure are further explained by the following detailed description, drawings and appended claims.

BRIEF DESCRIPTION OF THE DRAWING

The FIGURE is a schematic representation of paraffin dehydrogenation process using the process of the present disclosure.

Skilled artisans will appreciate that elements in the drawings are illustrated for simplicity and clarity and have not necessarily been drawn to scale. For example, the dimensions of some of the elements in the drawings may be exaggerated relative to other elements to help improve understanding of various embodiments of the present disclosure. Also, common but well-understood elements that are useful or necessary in a commercially feasible embodiment may not be depicted in order to facilitate a less obstructed view of these various embodiments of the present disclosure.

Definitions

The following detailed description is merely exemplary in nature and is not intended to limit the application and uses of the embodiment described. Furthermore, there is no intention to be bound by any theory presented in the preceding background or the following detailed description.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "bypass" means that the object is out of downstream communication with a bypassing subject at least to the extent of bypassing.

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1$, $C_2$, $C_3$ ... $C_n$ where "n" represents the number of carbon atoms in the one or more hydrocarbon molecules. Furthermore, a superscript "+" or "−" may be used with an abbreviated one or more hydrocarbons notation; e.g., $C_{3+}$ or $C_{3-}$, which is inclusive of the abbreviated one or more hydrocarbons. As an example, the abbreviation "$C_{3+}$" means one or more hydrocarbon molecules of three carbon atoms and/or more. In addition, the term "stream" may be applicable to other fluids, such as aqueous and non-aqueous solutions of alkaline or basic compounds, such as sodium hydroxide.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column. Alternatively, a stripping stream may be used for heat input near the bottom of the column.

As used herein, the term "rich" can mean that the outlet stream has a greater concentration of the indicated component than in the inlet stream to a vessel.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator which latter may be operated at higher pressure.

DETAILED DESCRIPTION

The process described herein is particularly useful for maintaining the $H_2$/HC ratio in a REC and a series of expanders and separation vessels commonly referred to as a cold box separation unit while enabling a dehydrogenation reactor to operate at a lower $H_2$/HC ratio. Applicants have developed an improved process of passing a portion of a recycle hydrogen stream, obtained from the cold box separation unit located downstream of the dehydrogenation reactor, to the reactor effluent compressor.

Conventionally, the propane dehydrogenation reactor was operated at a relatively higher $H_2$/HC ratio of 0.4 or higher. After developments in the dehydrogenation area, it was observed that by reducing the $H_2$/HC ratio in the dehydrogenation reactor a greater selectivity to propylene was achieved. Therefore, refiners are moving towards operating dehydrogenation reactors at a lower $H_2$/HC ratio. This leads to a reduction in the $H_2$/HC ratio of the dehydrogenation reactor effluent stream. If less hydrogen is present in the dehydrogenation reactor effluent stream the existing REC and cold box designs which rely on the hydrogen present within the dehydrogenation reactor effluent stream needs to be modified in order to achieve the desired product specifications. An improved process requires passing a portion of the recycle hydrogen stream to the REC. This increases the $H_2$/HC ratio of the stream processed in the compressor and the subsequent cold box separation unit thereby allowing the REC and cold box turbo expanders to operate at the same $H_2$/HC ratio as the original design and at the same time enables the paraffin dehydrogenation reactor to run at the reduced $H_2$/HC ratio.

The process comprises passing a feed stream comprising hydrocarbons and hydrogen to a dehydrogenation reactor at dehydrogenation conditions to provide a dehydrogenation reactor effluent. The dehydrogenation reactor effluent is passed to a reactor effluent compressor to provide a compressed hydrocarbon stream. The compressed hydrocarbon stream is passed to a cold box separation unit to provide an olefin stream and a recycle hydrogen stream. A return portion of the recycle hydrogen stream is passed to the reactor effluent compressor. This improved process allows the reactor effluent compressor and cold box turbo expanders to operate at the same $H_2$/HC ratio as the original design and at the same time enables the paraffin dehydrogenation reactor to run at reduced $H_2$/HC ratio.

An improved paraffin dehydrogenation process has been developed. In particular, the process is for the conversion of propane into propylene. An example of a process 100 is shown in the FIGURE which includes a dehydrogenation step, a compression step, a series of cryogenic separation steps. As shown in the FIGURE, the integrated process and apparatus 100 includes a dehydrogenation reactor 105, a reactor effluent compressor 110, and a cold box separation unit 170 comprising a cold combined feed exchanger 115, a series of separators 120, 130, 140 and 150, a series of turbo expanders 125, 135 and 145.

As shown in the FIGURE, a fresh hydrocarbon stream in a line 5 is passed to the dehydrogenation reactor 105. In an embodiment, the fresh hydrocarbon stream 5 is mixed with a charge portion stream comprising hydrogen in a line 50 to provide a combined feed stream in a line 8. The combined feed stream 8 may be pre-heated in the cold combined feed exchanger 115 to provide a pre-heated feed stream 10 before it passes to the dehydrogenation reactor 105. The pre-heated feed stream comprises hydrogen and paraffins.

The fresh hydrocarbon stream comprises propane. In some embodiments, the fresh hydrocarbon stream comprises other light paraffins such as butane, isobutane, iso-pentane or pentane. In some embodiments, the fresh hydrocarbon stream comprises at least one paraffin having 2 to 30 carbon atoms. The hydrogen-to-hydrocarbon molar ratio of the feed stream is in a range of 0.01 to 0.4.

The pre-heated feed stream is contacted with a dehydrogenation catalyst in the dehydrogenation reactor 105 maintained at dehydrogenation conditions to produce a dehydrogenation reactor effluent stream comprising hydrogen, unconverted paraffins, and olefins in a line 12. The dehydrogenation reactor 105 may be a reaction zone that includes multi-stages or multiple reactors, often in series.

A light paraffin dehydrogenation process utilizes a highly selective platinum-based catalyst system. One example of a suitable catalyst light paraffin dehydrogenation process may be a. catalyst composite comprises a Group VIII noble metal component, a Group IA or IIA metal component, and a component selected from the group consisting of tin, germanium, lead, indium, gallium, thallium, or mixtures thereof, all on an alumina support. A heavy paraffin dehydrogenation process uses a selective platinum catalyst.

Dehydrogenation conditions include a temperature of from about 400° to about 900° C., a pressure of from about 0.01 to about 10 atmospheres absolute, and a liquid hourly space velocity (LHSV) of from about 0.1 to about 100 hr$^{-1}$. Generally, for normal paraffins, the lower the molecular weight, the higher the temperature required for comparable conversion. The pressure in the dehydrogenation reactor 105 is maintained as low as practicable, consistent with equipment limitations, to maximize the chemical equilibrium advantages. A light paraffin dehydrogenation process will typically be carried out at a lower pressure than a heavy paraffin dehydrogenation process.

The dehydrogenation reactor effluent stream, exiting the dehydrogenation reactor in line 12, is compressed in the REC 110 to provide a compressed hydrocarbon stream in a line 18. The reactor effluent compressor may have two-stages or three-stages of compression. The dehydrogenation reactor effluent stream is compressed at a pressure of about 1 to about 2 MPa (a) and at a temperature of about 120° to about 150° C. The compressor increases the pressure of the dehydrogenation reactor effluent stream exiting the reactor, which helps in the separation of a gaseous phase incorporating hydrogen and a liquid phase incorporating the unconverted hydrocarbons and the reaction products in the cold box separation unit 170.

The compressed hydrocarbon stream 18 is passed to the cold box separation unit 170 to provide a liquid hydrocarbon product stream comprising olefins in a line 64 and a recycle hydrogen stream in a line 48, and a net gas hydrogen stream in a line 52. The cold box separation unit 170 includes the cold combined feed exchanger 115, a high-pressure separator 120, an intermediate pressure separator 130, a low-pressure separator 140, a net gas separator 150 and a series of turboexpanders 125, 135 and 145. The liquid hydrocarbon product stream is separated from hydrogen and byproduct methane, by condensation in the cold box separation unit 170.

The compressed hydrocarbon stream 18 is cooled in the cold combined feed exchanger 115 of the cold box separation unit 170. In the cold combined feed exchanger 115, heat exchange takes place between the compressed hydrocarbon stream 18 and the combined feed stream 8 such that the compressed hydrocarbon stream is cooled and the combined feed stream is pre-heated. The cooled hydrocarbon stream in a line 20 is then taken to a series of separators and turbo expanders present in the cold box separation unit 170 to provide the liquid hydrocarbon product stream in a line 64 comprising olefins, the recycle hydrogen stream 48 and the net gas hydrogen stream 52. The net gas hydrogen stream may comprise methane.

The cooled hydrocarbon stream 20 is passed to the high-pressure separator 120 to separate a high-pressure separator overhead stream comprising hydrogen and methane in a line 22 from a high-pressure separator bottoms stream comprising hydrocarbons in a line 24. The high-pressure separator 120 may operate at a pressure of about 1.1 to about 1.4 MPa and at a temperature of about −80° C. to about −100° C.

The high-pressure separator overhead stream 22 is passed to a turbo expander 125 for expansion and cooling. The expanded and cooled stream is then passed to the intermediate separator 130 to further separate hydrocarbons in an intermediate separator bottoms stream in a line 34. The intermediate separator 130 may operate at a pressure of about 0.7 to about 1.1 MPa and at a temperature of about −100° C. to about −130° C.

A first portion in a line 36 of an intermediate separator overhead stream in a line 32 is taken to a net gas cooler 145. The cooled first portion is then taken to the net gas separator 150 to provide the net gas hydrogen stream in line 52 and a net gas separator bottoms stream in a line 54 comprising a hydrocarbon fraction. The net gas separator 150 may operate at a pressure of about 0.4 to about 0.7 MPa and at a temperature of about −100° C. to about −130° C.

A second portion in a line 38 of the intermediate separator overhead stream 32 is passed to a turbo expander 135 for further expansion and cooling. The cooled second portion is then passed to the low-pressure separator 140 to further remove the hydrocarbons in a low-pressure separator bottoms stream in a line 44 and recover a hydrogen-rich stream in an overhead line 42. The low-pressure separator 140 may operate at a pressure of about 0.3 to about 0.4 MPa and at a temperature of about −130° C. to about −145° C. The hydrogen-rich stream 42 may be cooled in the net gas cooler 145 to provide the recycle hydrogen stream 48.

The hydrocarbon fractions in the separator bottoms streams in lines 24, 34, 44 and 54 are collected in a liquid hydrocarbon product stream in the line 64. The liquid hydrocarbon product stream in the line 64 may be further separated by means of an unshown, suitable fractionation scheme to recover unconverted hydrocarbons and product olefins comprising propylene. The unconverted hydrocarbons may be recycled to the dehydrogenation reactor 105. The net gas hydrogen stream in line 52 can optionally be purified and recycled or exported as hydrogen product or can be used as a fuel source a refinery complex.

The recycle hydrogen stream in line 48 is split into a return portion stream in a line 56 and the charge portion stream in a line 50. This split is done upstream of the cold combined feed exchanger 115 such that the fresh hydrocarbon stream in line 5 is mixed with the charge portion hydrogen stream 50 to provide the combined feed stream in line 8. The combined feed stream in line 8 may be pre-heated in the cold combined feed exchanger 115 before it passes to the dehydrogenation reactor 105 in line 10.

The return portion stream in the line 56 is combined with dehydrogenation reactor effluent stream in the line 12 to provide an enriched stream in line 16. The H$_2$/HC ratio of the enriched stream in the line 16 enriched with the return portion stream in line 56 of the recycle hydrogen stream is greater than the H$_2$/HC ratio of the dehydrogenation reactor effluent in line 12. The enriched stream in line 16 is then passed to the REC 110. In an embodiment, the return portion stream 56 may be pre-heated in the cold combined feed exchanger 115. The pre-heated return portion stream in a line 58 is combined with dehydrogenation reactor effluent stream 12 to provide the enriched stream 16.

EXAMPLE

Conventionally, the dehydrogenation reactor used to operate at a H$_2$/HC ratio of about 0.4 or higher. Applicants simulated a dehydrogenation process where the reactor is operating at a H$_2$/HC ratio of 0.5. In this simulated Base Case, a propane feed was passed to a dehydrogenation reactor operating at a H$_2$/HC ratio of 0.5 to obtain the dehydrogenation reactor effluent comprising 42-46 mol % hydrogen and 54-58 mol % hydrocarbons. The H$_2$/HC ratio of dehydrogenation reactor effluent entering the REC will vary between 0.72-0.8. This dehydrogenation reactor effluent was passed directly to the REC.

Applicants also simulated Scenario 1 and Scenario 2 of a dehydrogenation process operating at a $H_2/HC$ ratio of less than 0.4 to demonstrate the capability of described apparatus and process. In Scenario 1, the dehydrogenation reactor is operating at a $H_2/HC$ ratio of less than 0.4 with no hydrogen recycle to dehydrogenation reactor effluent. In Scenario 2, the dehydrogenation reactor is operating at a $H_2/HC$ ratio of less than 0.4 with a hydrogen recycle to dehydrogenation reactor effluent.

In the simulated Scenario 1, a propane feed was passed to a dehydrogenation reactor operating at low $H_2/HC$ ratio of less than 0.4 to obtain the dehydrogenation reactor effluent comprising 34-38 mol % Hz and 62-66 mol % hydrocarbons. This dehydrogenation reactor effluent was passed directly to the REC. The $H_2/HC$ ratio of the dehydrogenation reactor effluent entering the REC varied between 0.5-0.6 which is relatively low compared to the original design when the dehydrogenation reactor effluent entering the REC had a $H_2/HC$ ratio of 0.72-0.8 when the dehydrogenation reactor operated at high $H_2/HC$ ratio of greater than 0.4.

Scenario 2 differs in operation from Scenario 1 in that a portion of a recycle hydrogen stream was combined with the dehydrogenation reactor effluent to obtain an enriched stream. The enriched stream was then passed to the REC. The enriched stream comprised 42-46% $H_2$ and 54-58% of hydrocarbons. The $H_2/HC$ ratio of the enriched stream entering the REC varied between 0.72-0.8 which is higher than the Scenario 1 and same as that of the Base Case. Results are shown in the Table.

TABLE

| | Base Case (High $H_2/HC$ ratio of 0.5) | Scenario 1 (low $H_2/HC$ with no hydrogen recycle) | Scenario 2 (low $H_2/HC$ with hydrogen recycle) |
| --- | --- | --- | --- |
| Composition of dehydrogenation reactor effluent-stream 12 (mol %) | 42 to 46 $H_2$ 54 to 58 $C_{1+}$ | 34 to 38 $H_2$ 62 to 66 $C_{1+}$ | 34 to 38 $H_2$ 62 to 66 $C_{1+}$ |
| Composition of stream entering the REC - stream 16 (mol %) | 42 to 46 $H_2$ 54 to 58 $C_{1+}$ | 34 to 38 $H_2$ 62 to 66 $C_{1+}$ | 42 to 46 $H_2$ 54 to 58 $C_{1+}$ |

Applicants have found that by passing a portion of the recycle hydrogen stream to the REC it is feasible to operate the dehydrogenation reactor at a lower $H_2/HC$ ratio so as to achieve an improved selectivity towards olefin production while at the same time allowing the REC and cold box turbo expanders to operate at the same $H_2/HC$ ratio as the original design without requiring a capital investment in resizing the REC or the turboexpanders or separators in the cold box.

SPECIFIC EMBODIMENTS

While the following is described in conjunction with specific embodiments, it will be understood that this description is intended to illustrate and not limit the scope of the preceding description and the appended claims.

A first embodiment of the invention is a process for recovering hydrogen from dehydrogenation reactor effluent, the process comprising passing a feed stream comprising hydrocarbons and hydrogen to a dehydrogenation reactor maintained at dehydrogenation conditions to provide a dehydrogenation reactor effluent; passing the dehydrogenation reactor effluent to a reactor effluent compressor to provide a compressed hydrocarbon stream; passing the compressed hydrocarbon stream to a cold box separation unit to provide a liquid hydrocarbon product stream and a recycle hydrogen stream; and passing a return portion of the recycle hydrogen stream to the reactor effluent compressor. An embodiment of the invention is one, any or all of prior embodiments in this paragraph up through the first embodiment in this paragraph, further comprising mixing return portion of the recycle hydrogen stream with the dehydrogenation reactor effluent to provide an enriched stream and passing the enriched stream to the reactor effluent compressor. An embodiment of the invention is one, any or all of prior embodiments in this paragraph up through the first embodiment in this paragraph, wherein hydrogen to hydrocarbon ratio of the enriched stream is higher than hydrogen to hydrocarbon ratio of the dehydrogenation reactor effluent. An embodiment of the invention is one, any or all of prior embodiments in this paragraph up through the first embodiment in this paragraph, further comprising splitting the recycle hydrogen stream into the return portion and a charge portion of the recycle hydrogen stream. An embodiment of the invention is one, any or all of prior embodiments in this paragraph up through the first embodiment in this paragraph, wherein the return portion is 20-99 wt % of the recycle hydrogen stream and the charge portion is 1-80 wt % of the recycle hydrogen stream. An embodiment of the invention is one, any or all of prior embodiments in this paragraph up through the first embodiment in this paragraph, further comprising splitting the recycle hydrogen stream upstream of a cold combined feed exchanger located in the separation unit. An embodiment of the invention is one, any or all of prior embodiments in this paragraph up through the first embodiment in this paragraph, further comprising mixing the charge portion of the recycle hydrogen stream with a hydrocarbons stream upstream of the cold combined feed exchanger to provide the feed stream for the dehydrogenation reactor. An embodiment of the invention is one, any or all of prior embodiments in this paragraph up through the first embodiment in this paragraph, further comprising exchanging heat between the feed stream and the compressed hydrocarbon stream in the cold combined feed exchanger. An embodiment of the invention is one, any or all of prior embodiments in this paragraph up through the first embodiment in this paragraph, wherein hydrogen to hydrocarbon ratio of the feed stream is in the range of 0.01 to 0.4.

A second embodiment of the invention is a process for recovering hydrogen from dehydrogenation reactor effluent, the process comprising passing a feed stream comprising hydrocarbons and hydrogen to a dehydrogenation reactor maintained at dehydrogenation conditions to provide a dehydrogenation reactor effluent; passing the dehydrogenation reactor effluent to a reactor effluent compressor to provide a compressed hydrocarbon stream; passing the compressed hydrocarbon stream to a cold box separation unit to provide a liquid hydrocarbon product stream and a recycle hydrogen stream; and mixing a return portion of the recycle hydrogen stream with the dehydrogenation reactor effluent to provide an enriched stream and passing the enriched stream to the reactor effluent compressor. An embodiment of the invention is one, any or all of prior embodiments in this paragraph up through the second embodiment in this paragraph, wherein hydrogen to hydrocarbon ratio of the enriched stream is higher than hydrogen to hydrocarbon ratio of the dehydrogenation reactor effluent. An embodiment of the invention is one, any or all of prior embodiments in this paragraph up through the second embodiment in this paragraph, further comprising splitting the recycle hydrogen stream into the return portion and a charge portion of the recycle hydrogen stream at upstream of a cold combined feed exchanger located in the separation unit. An embodiment of the invention is one, any or all of prior embodiments in this paragraph up through the second embodiment in this paragraph, further comprising mixing the charge portion of the recycle hydrogen stream with a hydrocarbons stream upstream of the cold combined feed exchanger to provide the feed stream for the dehydrogenation reactor. An embodiment of the invention is one, any or all of prior embodiments in this paragraph up through the second embodiment in this paragraph, wherein hydrogen to hydrocarbon ratio of the feed stream is in the range of 0.01 to 0.4.

A third embodiment of the invention is an apparatus for recovering hydrogen from dehydrogenation reactor effluent comprising a dehydrogenation reactor operating under dehydrogenation conditions configured to selectively dehydrogenate a feed stream comprising hydrocarbons and hydrogen and provide a dehydrogenation reactor effluent; a reactor effluent compressor in fluid communication with the dehydrogenation reactor via the dehydrogenation reactor effluent and configured to compress the dehydrogenation reactor effluent to provide a compressed hydrocarbon stream; a cold box separation unit in fluid communication with the reactor effluent compressor via the compressed hydrocarbon stream and configured to provide a liquid hydrocarbon product stream and a recycle hydrogen stream; and the reactor effluent compressor is in fluid communication with the cold box separation unit via a return portion of the recycle hydrogen stream. An embodiment of the invention is one, any or all of prior embodiments in this paragraph up through the third embodiment in this paragraph, wherein the cold box separation unit comprises of a heat exchangers including the cold combined feed exchanger, multiple separation vessels, expanders. An embodiment of the invention is one, any or all of prior embodiments in this paragraph up through the third embodiment in this paragraph, wherein the cold combined feed exchanger is in fluid communication with the reactor effluent compressor via the compressed hydrocarbon stream. An embodiment of the invention is one, any or all of prior embodiments in this paragraph up through the third embodiment in this paragraph, wherein a split is present upstream of the cold combined feed exchanger to divide the recycle hydrogen stream into the return portion and a charge portion. An embodiment of the invention is one, any or all of prior embodiments in this paragraph up through the third embodiment in this paragraph, wherein the reactor effluent compressor is in fluid communication with the cold combined feed exchanger via the return portion of the recycle hydrogen stream. An embodiment of the invention is one, any or all of prior embodiments in this paragraph up through the third embodiment in this paragraph, wherein the dehydrogenation reactor is in fluid communication with the cold combined feed exchanger via the feed stream obtained by mixing a hydrocarbons stream with the charge portion of the recycle hydrogen stream upstream of the cold combined feed exchanger.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for recovering hydrogen from dehydrogenation reactor effluent, the process comprising:
   passing a feed stream comprising hydrocarbons and hydrogen to a dehydrogenation reactor maintained at dehydrogenation conditions to provide a dehydrogenation reactor effluent;
   passing the dehydrogenation reactor effluent to a reactor effluent compressor to provide a compressed hydrocarbon stream;
   passing the compressed hydrocarbon stream to a cold box separation unit to provide a liquid hydrocarbon product stream and a recycle hydrogen stream;
   splitting the recycle hydrogen stream upstream of a cold combined feed exchanger located in the separation unit; and
   passing a return portion of the recycle hydrogen stream to the reactor effluent compressor.

2. The process of claim 1, further comprising mixing the return portion of the recycle hydrogen stream with the dehydrogenation reactor effluent to provide an enriched stream and passing the enriched stream to the reactor effluent compressor.

3. The process of claim 2, wherein hydrogen to hydrocarbon ratio of the enriched stream is higher than hydrogen to hydrocarbon ratio of the dehydrogenation reactor effluent.

4. The process of claim 1, further comprising splitting the recycle hydrogen stream into the return portion and a charge portion of the recycle hydrogen stream.

5. The process of claim 4, wherein the return portion is 20-99 wt % of the recycle hydrogen stream and the charge portion is 1-80 wt % of the recycle hydrogen stream.

6. The process of claim 4, further comprising mixing the charge portion of the recycle hydrogen stream with a hydrocarbons stream upstream of the cold combined feed exchanger to provide the feed stream for the dehydrogenation reactor.

7. The process of claim 6, further comprising exchanging heat between the feed stream and the compressed hydrocarbon stream in the cold combined feed exchanger.

8. The process of claim 1, wherein hydrogen to hydrocarbon ratio of the feed stream is in the range of 0.01 to 0.4.

9. A process for recovering hydrogen from dehydrogenation reactor effluent, the process comprising:
   passing a feed stream comprising hydrocarbons and hydrogen to a dehydrogenation reactor maintained at dehydrogenation conditions to provide a dehydrogenation reactor effluent;
   passing the dehydrogenation reactor effluent to a reactor effluent compressor to provide a compressed hydrocarbon stream;
   passing the compressed hydrocarbon stream to a cold box separation unit to provide a liquid hydrocarbon product stream and a recycle hydrogen stream;
   splitting the recycle hydrogen stream upstream of a cold combined feed exchanger located in the separation unit; and
   mixing a return portion of the recycle hydrogen stream with the dehydrogenation reactor effluent to provide an enriched stream and passing the enriched stream to the reactor effluent compressor.

10. The process of claim 9, wherein hydrogen to hydrocarbon ratio of the enriched stream is higher than hydrogen to hydrocarbon ratio of the dehydrogenation reactor effluent.

11. The process of claim 9, further comprising splitting the recycle hydrogen stream into the return portion and a charge portion of the recycle hydrogen stream.

12. The process of claim 11, further comprising mixing the charge portion of the recycle hydrogen stream with a hydrocarbons stream upstream of the cold combined feed exchanger to provide the feed stream for the dehydrogenation reactor.

13. The process of claim 9, wherein hydrogen to hydrocarbon ratio of the feed stream is in the range of 0.01 to 0.4.

14. An apparatus for recovering hydrogen from dehydrogenation reactor effluent comprising:
  a dehydrogenation reactor operating under dehydrogenation conditions configured to selectively dehydrogenate a feed stream comprising hydrocarbons and hydrogen and provide a dehydrogenation reactor effluent;
  a reactor effluent compressor in fluid communication with the dehydrogenation reactor via the dehydrogenation reactor effluent and configured to compress the dehydrogenation reactor effluent to provide a compressed hydrocarbon stream;
  a cold box separation unit comprising of a cold combined feed exchanger in fluid communication with the reactor effluent compressor via the compressed hydrocarbon stream and configured to provide a liquid hydrocarbon product stream and a recycle hydrogen stream;
  a split is present upstream of the cold combined feed exchanger to divide the recycle hydrogen stream; and
  the reactor effluent compressor is in fluid communication with the cold box separation unit via a return portion of the recycle hydrogen stream.

15. The apparatus of claim 14, wherein the cold box separation unit comprises of a plurality of heat exchangers including the cold combined feed exchanger, and a plurality of separation vessels and expanders.

16. The apparatus of claim 15, wherein the cold combined feed exchanger is in fluid communication with the reactor effluent compressor via the compressed hydrocarbon stream.

17. The apparatus of claim 15, wherein the split is to divide the recycle hydrogen stream into the return portion and a charge portion.

18. The apparatus of claim 15, wherein the reactor effluent compressor is in fluid communication with the cold combined feed exchanger via the return portion of the recycle hydrogen stream.

19. The apparatus of claim 15, wherein the dehydrogenation reactor is in fluid communication with the cold combined feed exchanger via the feed stream obtained by mixing a hydrocarbons stream with the charge portion of the recycle hydrogen stream upstream of the cold combined feed exchanger.

* * * * *